US007139688B2

(12) United States Patent
Aggarwal et al.

(10) Patent No.: US 7,139,688 B2
(45) Date of Patent: Nov. 21, 2006

(54) METHOD AND APPARATUS FOR CLASSIFYING UNMARKED STRING SUBSTRUCTURES USING MARKOV MODELS

(75) Inventors: Charu C. Aggarwal, Ossining, NY (US); Philip Shi-Lung Yu, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 616 days.

(21) Appl. No.: 10/600,690

(22) Filed: Jun. 20, 2003

(65) Prior Publication Data

US 2004/0260663 A1    Dec. 23, 2004

(51) Int. Cl.
*G06F 17/50* (2006.01)
*G06F 17/28* (2006.01)
*G10L 15/14* (2006.01)

(52) U.S. Cl. .................. 703/2; 704/254; 704/255; 706/20

(58) Field of Classification Search .............. 703/2, 703/22; 704/9, 254, 255, 260; 382/229; 706/20
See application file for complete search history.

(56) References Cited

U.S. PATENT DOCUMENTS 5,477,451 A * 12/1995 Brown et al. ................ 704/9

| | | | | |
|---|---|---|---|---|
| 5,806,032 A * | 9/1998 | Sproat | ............ | 704/255 |
| 2003/0187643 A1* | 10/2003 | Van Thong et al. | ........ | 704/254 |
| 2003/0216919 A1* | 11/2003 | Roushar | ............ | 704/260 |
| 2005/0191688 A1* | 9/2005 | Selifonov et al. | ............ | 435/6 |
| 2005/0226512 A1* | 10/2005 | Napper | ............ | 382/229 |

OTHER PUBLICATIONS

C.C. Aggarwal, "On Effective Classification of Strings with Wavelets," ACM KDD Conference, 10 pages, 2002.
G.A. Churchill, "Stochastic Models for Heterogeneous DNA Sequences," Bulletin of Mathematical Biology, vol. 51, No. 1, pp. 79-94, 1989.
M. Deshpande et al., "Evaluation of Techniques for Classifying Biological Sequences," Technical Report, TR 01-33, University of Minnesota, pp. 1-8, 2001.
S. Subbiah et al., "A Method for Multiple Sequence Alignment with Gaps," Journal of Molecular Biology, vol. 209, pp. 539-548, 1989.
D. Haussler et al., "Protein Modeling Using Hidden Markov Models: Analysis of Globins," Technical Report UCSC-CRL-92-23, University of California at Santa Cruz Comp. Sci., 12 pages, 1993.

* cited by examiner

*Primary Examiner*—Thai Phan
(74) *Attorney, Agent, or Firm*—Ryan, Mason & Lewis, LLP

(57) ABSTRACT

A technique for structurally classifying substructures of at least one unmarked string utilizing at least one training data set with inserted markers identifying labeled substructures. A model of class labels and substructures within strings of the training data set is first constructed. Markers are then inserted into the unmarked string, identifying substructures similar to substructures within strings of the training data set by using the model. Finally, class labels of the substructures in the unmarked string similar to substructures within strings of the training data set are predicted using the model.

43 Claims, 7 Drawing Sheets

METHOD AND APPARATUS FOR CLASSIFYING UNMARKED STRING SUBSTRUCTURES USING MARKOV MODELS

FIELD OF THE INVENTION

The present invention is related to a technique for classifying string substructures and, more particularly, for identifying the classes of specific fragments of the strings using a model such as a Hidden Markov Model.

BACKGROUND OF THE INVENTION

A number of applications provide data in string format, including market basket analysis, customer tracking, DNA (deoxyribonucleic acid) analysis, and text. In many cases it is desirable to find subpatterns in these strings having particular formats. The traditional classification technique is defined as follows: A set of strings are given, each of which is labeled with a class drawn from the set $C_1 \ldots C_k$. The correct classification label is then found for a given test data record for which the class label was originally unknown. This traditional classification technique only concerns the classification of entire strings, and does not address the significantly more complex problem of finding particular classes of substructures within strings.

In many applications the problem of finding substructures in strings is significantly more important than that of classifying the string itself. For example:

(1) In a genome application different kinds of protein sequences may be sought, which are embedded in very long patterns. A given pattern may contain one or multiple occurrences of such a sequence substructure. The number and types of such occurrences may not even be known a priori.

(2) In a text application it may be desirable to find particular segments or paragraphs which belong to a particular topic or satisfy other conditions, which cannot be expressed in closed form, but only in the form of examples.

The examples above can present complex variations in which the same data can have different classes of substructures and in which some classes of substructures are embedded within others. This often occurs in the biological domain. In a text article certain segments of interest may be divided into further subsections of a particular kind. Thus, there may be a hierarchical aspect to the class behavior of the data. This illustrates a generalized classification problem since the correct classification of a given substructure must be found and the exact location and extent of the substructure in the data must be determined.

The standard classification problem for strings has been studied in the computational biology, database and data mining fields, see, e.g., reports such as C. C. Aggarwal, "On Effective Classification of Strings with Wavelets," ACM KDD Conference, 2002; G. A. Churchill, "Stochastic Models for Heterogeneous DNA Sequences," Bull. Math Biol, 59, pp. 79–91, 1989; M. Deshpande. et al., "Evaluation of Techniques for Classifying Biological Sequences," Technical report, TR 01–33, University of Minnesota, 2001; S. Subbiah et al., "A Method for Multiple Sequence Alignment with Gaps," Journal of Molecular Biology, 209, pp. 539–548, 1989; and M. S. Waterman, "Sequence Alignments," In: Mathematical Methods for DNA Sequences, Waterman M. S. ed. CRC Press, 1989. A good comparative study of the most important classification methods for the strings can be found in M. Deshpande et al., "Evaluation of Techniques for Classifying Biological Sequences," Technical report, TR 01–33, University of Minnesota, 2001. Recently, a wavelet classification method for the string problem was discussed in C. C. Aggarwal, "On Effective Classification of Strings with Wavelets," ACM KDD Conference, 2002. This technique has been shown to be more effective than other string classifiers discussed by M. Deshpande et al.

The nature of substructure mining is inherently more difficult than standard classification. Standard classification methods such as rule based methods, decision trees, and nearest neighbor classifiers are designed only for the task of labeling entire records. These methods cannot be easily extended to the generalized substructure classification problem which is inherently more complex in its nature.

Thus, there exists a need for techniques which overcome the drawbacks associated with the approaches described above, as well as drawbacks not expressly described above, and which thereby provide more efficient and scalable solutions to the problems associated with string substructure classification.

SUMMARY OF THE INVENTION

The present invention provides techniques for classifying string substructures and, more particularly, for identifying the classes of specific fragments of the strings using a model such as a Hidden Markov Model.

For example, in one aspect of the invention, a technique for classifying at least one unmarked string, using a training data set with inserted markers identifying labeled substructures, comprises the following steps. First, a model is constructed comprising the class labels and substructures, within the strings of the training data set. Then, the model is used to insert markers in the unmarked string identifying substructures similar to substructures within strings of the training data set. Finally, the model predicts class labels of substructures in the unmarked string similar to substructures within strings of the training data set.

In order to solve the generalized substructure classification problem a model such as a Hidden Markov Model may be used. A traditional problem of Hidden Markov Models has been making them scalable for very large databases. The parameter estimation procedure of a Hidden Markov Model usually requires an iterative expectation maximization procedure, which is computationally expensive and may require a large number of passes for disk resident data. In accordance with the present invention, the models may be constructed so that the parameters can be accurately estimated both from the computational and I/O (input/output) perspective. The entire training procedure may comprise a single database scan.

Advantageously, the inventive technique makes the process of substructure mining and labeling easier. Additionally, the inventive technique can be applied to very large disk resident databases since the training procedure requires only a single database scan.

These and other objects, features, and advantages of the present invention will become apparent from the following detailed description of illustrative embodiments thereof, which is to be read in connection with the accompanying drawings.

DETAILED DESCRIPTION OF PREFERRED EMBODIMENTS

The following description will illustrate the invention using an exemplary data processing system architecture. It should be understood, however, that the invention is not limited to use with any particular system architecture. The invention is instead more generally applicable to any data processing system in which it is desirable to perform efficient, effective, and scalable string substructure classification.

As will be illustrated in detail below, the present invention introduces a technique for classifying string substructures, and more particularly, for identifying the classes of specific fragments of the strings using a model such as a Hidden Markov Model.

Figure 1:
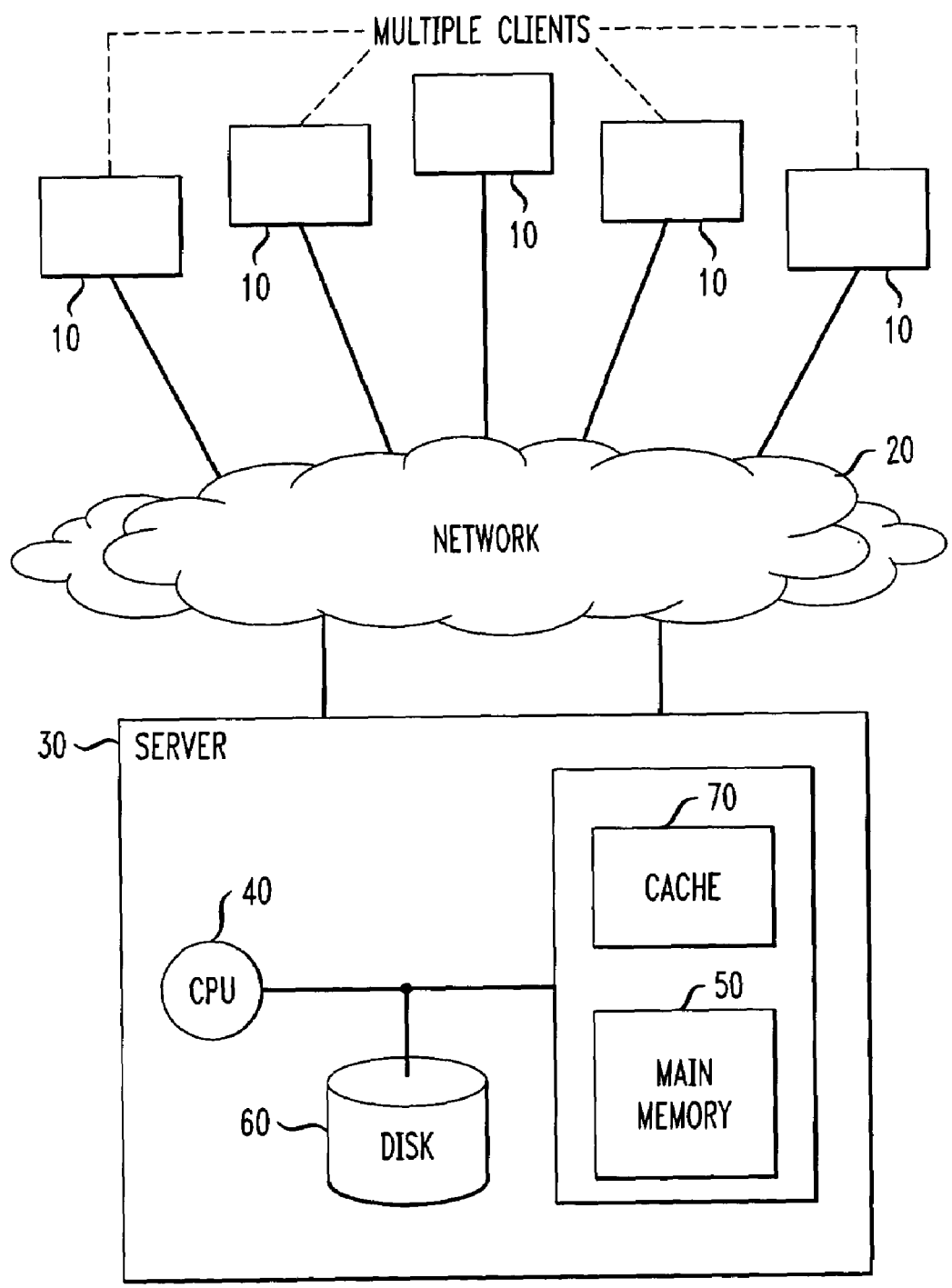
FIG. 1 is a block diagram illustrating a hardware implementation suitable for employing methodologies, according to an embodiment of the present invention.

Referring initially to FIG. 1, a block diagram illustrates a hardware implementation suitable for employing methodologies according to an embodiment of the present invention. As illustrated, an exemplary system comprises client devices 10 coupled via a large network 20 to a server 30. Server 30 may comprise a central processing unit (CPU) 40 coupled to a main memory 50 and a disk 60. Server 30 may also comprise a cache 70 in order to speed up calculations. Multiple clients 10 can interact with server 30 over large network 20. It is to be appreciated that network 20 may be a public information network such as, for example, the Internet or World Wide Web, however, the clients and server may alternatively be connected via a private network, a local area network, or some other suitable network.

The string substructure classification computations of the invention are performed at CPU 40 on server 30 and sent to client devices 10. It is to be understood that an individual client device 10 issues the requests for classification and also supplies the data sets to server 30. However, all or portions of the data sets to be processed may already be available at server 30 (on disk 60), or may be accessible by server 30. Main memory 50 is used in order to store some or all of the intermediate results performed during the computations. Results of these computations are then returned to the requesting client device 10 and presented to the client.

In one preferred embodiment software components including instructions or code for performing the methodologies of the invention, as described herein, may be stored in one or more memory devices described above with respect to the server and, when ready to be utilized, loaded in part or in whole and executed by the CPU.

Hidden Markov Models (see, e.g., D. Haussler et al., "Protein Modeling using Hidden Markov Models: Analysis of Globins," Technical Report UCSC-CRL-92-23, University of California at Santa Cruz Comp. Sci., 1992) are important due to their applicability to modeling a wide range of complex phenomenon. A Hidden Markov Model describes a series of observations through a "hidden" stochastic process called a Markov chain. The model has a number of underlying states, which have transitions into one another with predefined probabilities. A probability distribution of symbols is associated with each state. For each transition a symbol is generated by using the probability distribution of symbols at the state that the system transitioned from. Each such transition may result in the generation of a symbol from a predefined alphabet. While the actual sequence of states is not observable (and is only a conceptual model), the sequence of symbols generated by the Hidden Markov Model are available to the user.

Figure 2:
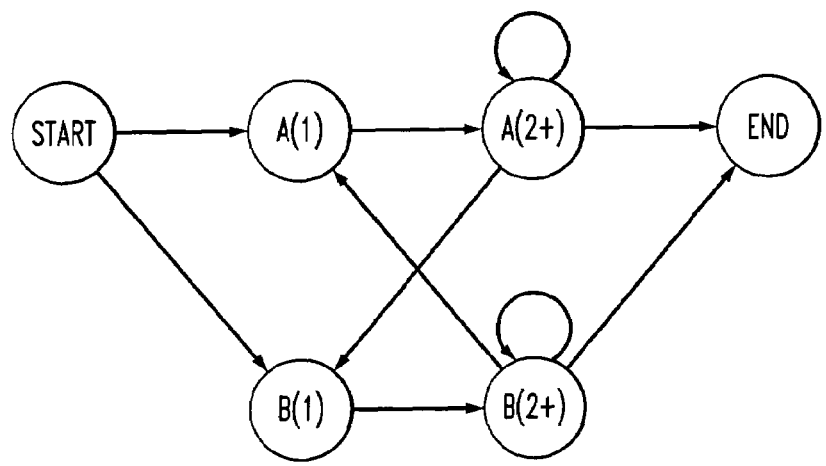
FIG. 2 is a flow diagram illustrating an example of a Markov Model, according to an embodiment of the present invention.

Referring now to FIG. 2, a flow diagram illustrates an example of a Markov model. Other than the START state and END state, the model contains 4 states labeled A(1), A(2+), B(1), and B(2+), respectively. This model represents sequences drawn from the alphabet {A, B}. A transition from either state A(1) or state A(2+) results in the generation of symbol A, whereas a transition from either state B(1) or state B(2+) results in the generation of symbol B. The topology of the model ensures that all sequences generated from the model contain alternating subsequences of two or more symbols of the same type. Thus, a valid sequence generated from this model would be AABBBAA, but not AABAA. For any given string the maximum probability path (product of corresponding transition probabilities and symbol generation probabilities) through the model reflects the level of correlation of the string to the model. In FIG. 2 the probability of any path generating the string AABAA is 0. By changing the symbol distribution and transition probabilities at the states it is possible to also change the nature of the sequences generated. Therefore, Markov Models are often used in computational biology for recognizing different classes of strings by estimating these parameters for a given training set. The actual topology of the Hidden Markov Model is dependent on the skill of the application domain expert.

In many cases it is possible to design the Markov Model so that it characterizes the natural behavior of the sequence. For example, in the particular model discussed in FIG. 2 the states implicitly count the current number of symbols of a particular kind that have been encountered at the present position in the sequence. Thus, the state A(2+) refers to the fact that two or more (consecutive) symbols of A have just been encountered in the sequence. In this case the Markov model is designed by using the fact that two or more symbols of a particular kind appear consecutively. More general models are possible and would vary in effectiveness depending upon the nature of the particular training data available.

The states of the Markov Model are denoted by $S=\{q_i \ldots q_N\}$. The initial state probabilities are denoted by $\pi(1) \ldots \pi(N)$. Therefore $\pi(i)$ is the probability that the system is in state i at the beginning of the stochastic process. It is clear that:

$$\sum_{(i=1)}^{N} \pi(i) = 1$$

The set of symbols from which the strings are constructed are denoted by $\Sigma=(\sigma_1 \ldots \sigma_l)$. For each state $q_j$ in S, a probability distribution characterizes the symbol being generated at the corresponding transition. This probability is denoted as the symbol $\sigma_i$ being generated in state $q_j$ by $b_j(\sigma_i)$. The probability of a transition from state $q_j$ to state $q_k$ is denoted by $a_{jk}$.

Each sequence of transitions in the Markov Model creates a sequence of symbols generated at the various states. The corresponding path P for the sequence of transitions is denoted as $i_0 \ldots i_{T+1}$, and the set of symbols generated at those states is denoted as $SS=\theta_1 \ldots \theta_{T+1}$. Then, using string segment G, the probability of the occurrence of path P is given by the product of the corresponding state transition and symbol generation probabilities. Therefore, the following expression is produced:

$$\text{Prob}(P,SS)=P(i_0, i_{T+1}, T+1, G)=\pi_{i_0}a_{i_0i_1}b_{i_1\theta_1}a_{i_1i_2} \ldots b_{i_{T-1}\theta_{T-1}}a_{i_{T-1}i_T}b_{i_T\theta_T}a_{i_Ti_{T+1}}$$

The above expression is simply the product of the probabilities of state transitions and corresponding symbol generations. While constructing a Hidden Markov Model with a particular training data set, parameters such as $a_{ij}$ and $b_j(.)$ need to be estimated from the data.

The classification technique begins by providing training data set D containing N strings $s_1 \ldots s_N$. A set of k class labels denoted by $C_1 \ldots C_k$ are also provided. Each string $s_i$ may have one or more substructures which satisfy the following properties:

(1) The substructure has a begin marker which indicates its first position in $s_i$;

(2) The substructure has an end marker which indicates its last position in $s_i$; and (3) The substructure has a label drawn from $C_1 \ldots C_k$ which indicates its class.

Training data set D is used to train a model to identify the substructures in unmarked strings. For a given test record x, the model is used to identify the following:

(1) The identity of the classes present in test record x as substructures; and (2) The location and extent of these substructures.

The classification methodology automatically inserts the appropriately labeled markers into the strings in order to identify the location and extent of the substructures in test record x.

Figure 3:
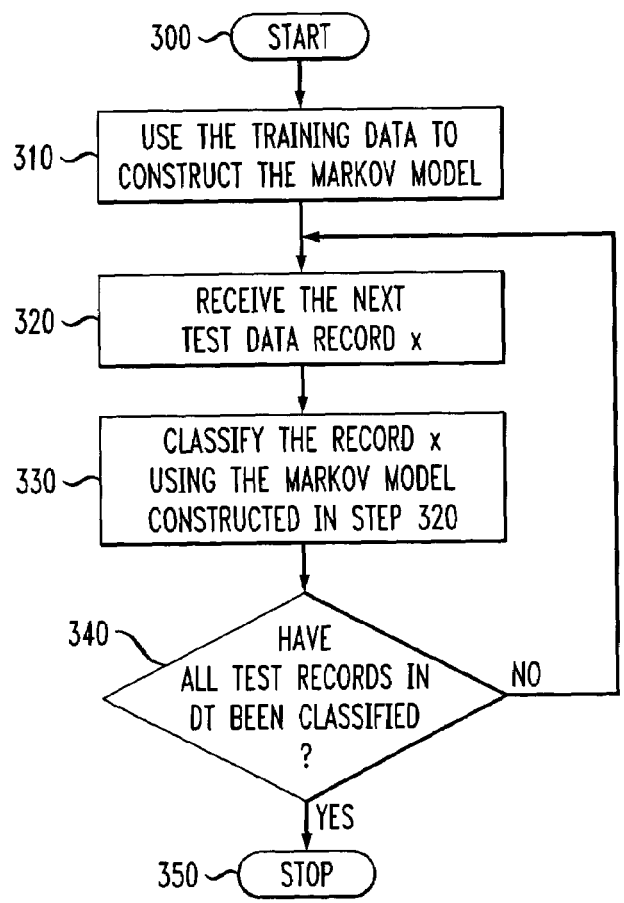
FIG. 3 is a flow diagram illustrating a string substructure classification methodology, according to an embodiment of the present invention.

Referring now to FIG. 3, a flow diagram illustrates a string substructure classification methodology, according to an embodiment of the present invention. The methodology begins at step 300 where training data set D is provided, which consists of strings having marked substructures. In step 310, training data set D is used to construct the Markov Model. This methodology is described in more detail in FIG. 5. In step 320, a test data record x is received from the test data set. In step 330, test data record x is classified using the model constructed in step 310. This methodology is described in more detail in FIG. 6. In step 340, the methodology checks whether all test records x have been classified. If all test records x have been classified the methodology terminates in step 350. If all records have not been classified the methodology returns to step 320.

Figure 4:
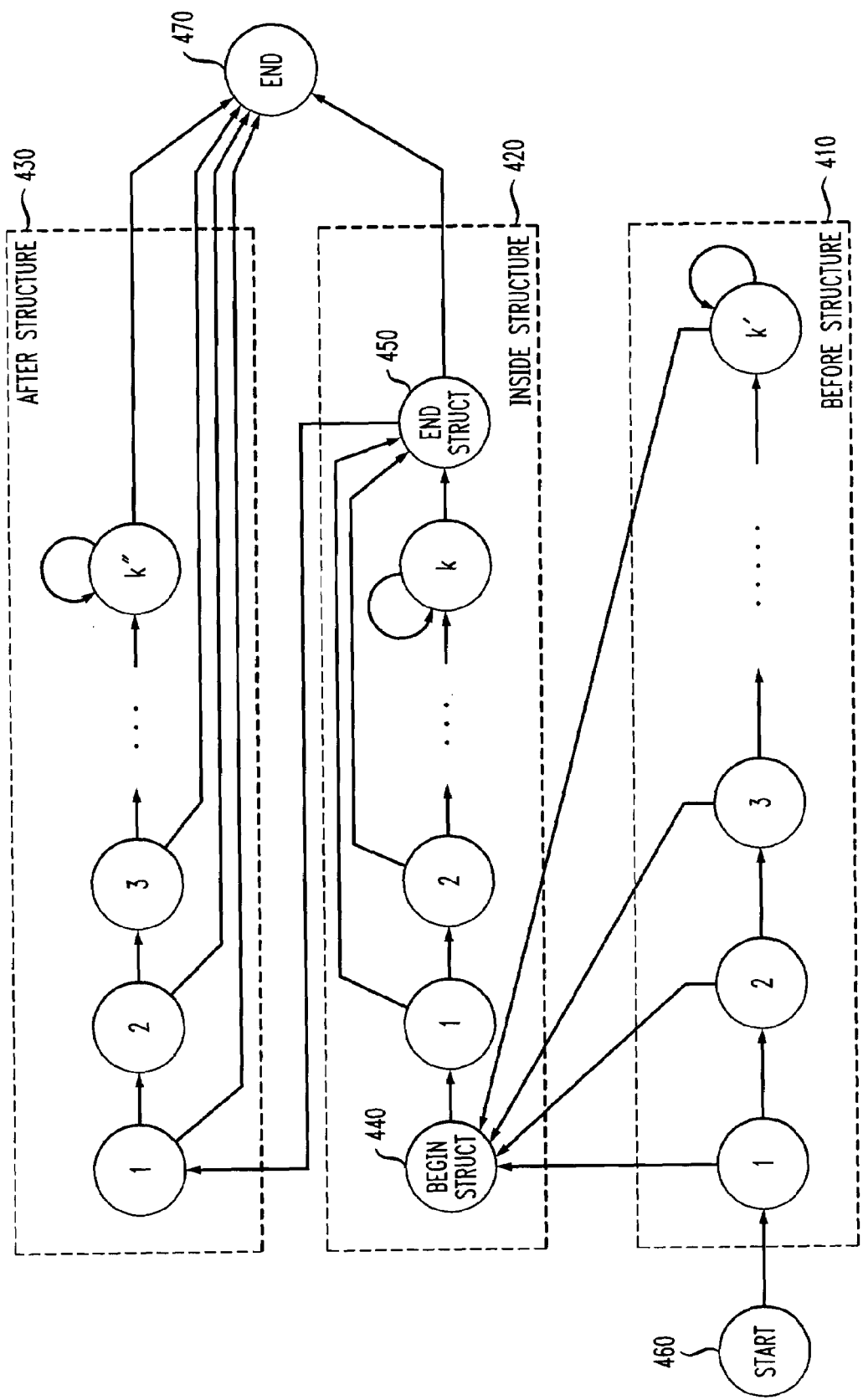
FIG. 4 is a flow diagram illustrating a Markov Model having three sets of states, according to an embodiment of the present invention.

Referring now to FIG. 4, a flow diagram illustrates a Markov Model having three sets of states, according to an embodiment of the present invention. This Markov Model illustrates a simple case when a single substructure is embedded within a string and may be constructed in step 310 of FIG. 3. The string is divided into three set of states: (1) the set before the begin marker outside the substructure, 410; (2) the set within the substructure itself, 420; and (3) the set after the end marker outside the substructure, 430. In order to transition from one set of states to another, either a begin marker 440 or an end marker 450 must be encountered. This is achieved by ensuring that the probability distribution of the symbols generated by the first and last states of the second set of states are the deterministic distributions corresponding to the "begin" and "end" markers. Therefore, the state marked as "begin struct" 440 always generates the symbol corresponding to the begin marker, whereas the state marked "end struct" 450 always generates the symbol corresponding to the end marker. Thus, the symbol set for the Markov Model is given by $\Sigma'=\Sigma+(\text{beg}_{str}, \text{end}_{str})$.

In addition, two constraints are imposed on matching a string with the Markov Model for all cases discussed in this invention:

(1) The initial set of state probabilities are chosen so that the beginning state is a START state 460. This is achieved by setting $\pi(i)=0$ for each state other than the START state. The initial set of state probabilities are set in step 520 of FIG. 5.

(2) After generation of all the symbols of the Hidden Markov Model, the system finishes in an END state 470.

Therefore, only those sequences in the Markov Model which begin at START state 460 and end at END state 470 are of interest. The constraint on the model finishing in END state 470 can also be imposed by appending a special termination marker at the end of each string which is generated only by END state 470.

Figure 5:
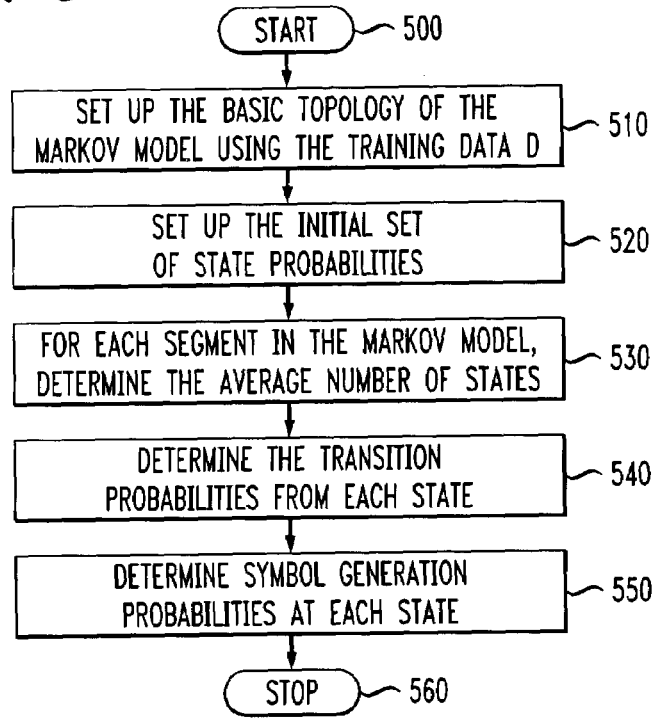
FIG. 5 is a flow diagram illustrating a Markov Model construction methodology, according to an embodiment of the present invention.

Referring now to FIG. 5, a flow diagram illustrates a Markov Model construction methodology, according to an embodiment of the present invention. This can be considered a detailed description of step 310 of FIG. 3. The methodology begins at step 500. Step 510 sets up the basic topology of the Markov Model using training data set D. Examples of different Markov Models are illustrated in FIGS. 4 and 7–9. The initial set of state probabilities are set in step 520. In step 530, the number of states in each segment of the string is determined. The portion inside the substructure contains k states. The portions before and after the substructure contain k' and k" states, respectively. The last symbol of each segment contains a self-looping state which is used to model the case when the length of the string in that segment is larger than the number of available states. The values of k, k', and k" are estimated using training data set D.

The effectiveness of the model depends considerably upon how these parameters are estimated. In order to perform this computation, the mean and standard deviation of the number of symbols inside, before, and after the substructure are found. The corresponding means are denoted by $\mu$, $\mu'$, and $\mu''$ respectively. The standard deviations are denoted by $\gamma$, $\gamma'$, and $\gamma''$ respectively. Then the parameters estimations for k, k' and k" are $\mu+r\gamma$, $\mu'+r\gamma'$, and $\mu''+r\gamma''$, respectively. Here r is a user-defined parameter.

Next, the transition and symbol generation probabilities are estimated in steps 540 and 550 respectively. This part of the parameter estimation is often a nontrivial task for a given Hidden Markov Model because the parameter estimation process requires an iterative expectation-maximization process which requires multiple passes over the data. This process is infeasible for most large databases because of the considerable disk I/O required for multiple data passes.

However, in the models discussed in this invention, the parameter estimation problem can be solved in a different way. The generated symbols of the "begin struct" and "end struct" states is deterministic with a probability of one. All Markov models discussed in this invention are designed so that the state to which each transition occurs belongs to one of two kinds of states: (1) the "begin struct" or "end struct" states which generate the begin markers and end markers deterministically; or (2) any of the other states which generate one of the symbols from the base alphabet.

Since the training data is provided with the "begin markers" and "end markers" specified in the strings, the exact sequence of transitions for each training data point can be known exactly irrespective of the transition and symbol generation probabilities. This is not the case for most Markov Models in which the paths are only known probabilistically, and in which the parameter estimation method uses iterative methods in order to maximize the accuracy of estimation. The models discussed in the present invention can easily estimate parameters by finding the unique path through the model for each training example. Once these paths have been determined, the following set of aggregate statistics are computed from the training data:

$A_{ij}$: number of times that a transition from state $q_i$ to state $q_j$ occurs over all unique paths for the different training sequences; and $B_i(\sigma_k)$: number of times that symbol $\sigma_k$ is observed in state $q_i$ over all unique paths for the different training sequences.

In the state i, there are N possible transitions out of it. If no data is available, then each possible transition out of state i has a probability of 1/N. Similarly, for a given transition, since l possible symbols can be generated, the probability of each possible symbol being generated by default is given by 1/l. When the amount of data available is small, it is desirable for the final probability to be a weighted combination of the default probability and the straightforward estimation using the data itself. For example, the transition probability $a'_{ij}$ using the data only is given by the following:

$$a'_{ij} = \frac{A_{ij}}{\sum_{j=1}^{N} A_{ij}}$$

The statistic in the numerator represents the number of transitions from state i to state j, whereas the statistic in the denominator represents the total number of transitions from state i. The methodology of FIG. 5 terminates at step 560.

Figure 6:
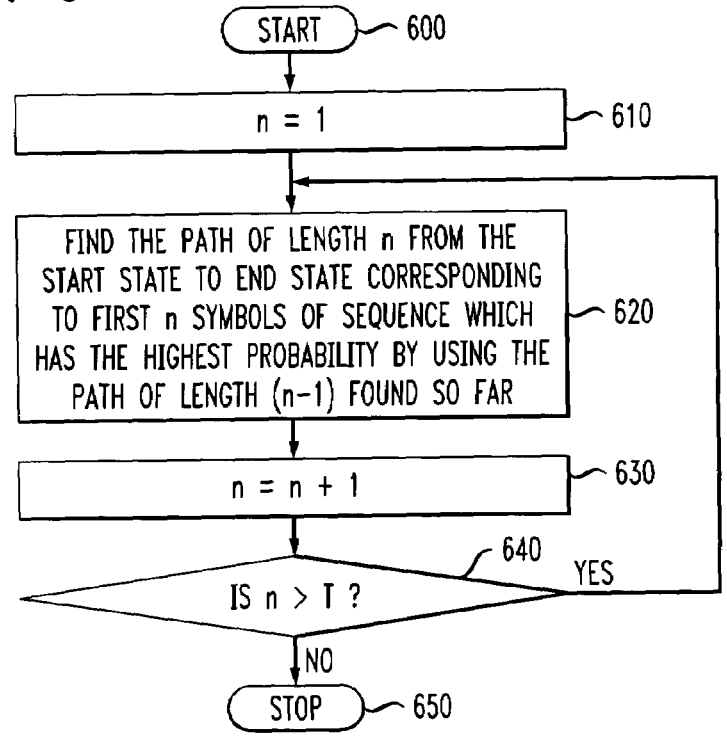
FIG. 6 is a flow diagram illustrating a test issuance classification methodology, according to an embodiment of the present invention.

Referring now to FIG. 6, a flow diagram illustrates a test data record classification methodology, according to an embodiment of the present invention. This can be considered a detailed description of step 330 of FIG. 3. Data records x are strings in which the positions of the begin and end markers have not been specified. As already shown, there is a single non-zero probability path through the Markov Model, once these positions have been specified.

For a given test data record x, it is determined where the begin and end markers should be inserted so that the probability of the unique path through the Markov Model is maximized. For the standard classification problems, as discussed in C. C. Aggarwal, "On Effective Classification of Strings with Wavelets," ACM KDD Conference, 2002, the test data record is completely specified. Multiple paths exists through the model, and the identity of the class label is decided by the maximum probability path. Regarding the present invention, for an incompletely specified string, it is determined where the marker labels are inserted so as to maximize the probability of the corresponding path through the Markov Model. It is possible to use a dynamic programming methodology which can optimize these placements.

The purpose of the dynamic programming methodology is to find paths of longer and longer length by increasing the path length by 1 in each iteration. The methodology begins at step 600. In step 610, the counter n is set to 1. This counter tracks the length of the path currently under consideration. The test data record is denoted by $\theta_1 \ldots \theta_T$. This test data record corresponds to a path through the Markov Model. Typically, this path will have length greater than T, but exactly T of the nodes on the path will correspond to symbols which are different from the "begin struct" and "end struct" labels. These states are denoted by $q_{i_1} \ldots q_{i_T}$. In addition, the first node on the path is the START state which corresponds to $q_{i_0}$, and the last node $q_{i_{T+1}}$ is the END state. The sequence of states, $q_{i_1} \ldots q_{i_{T+1}}$, may not necessarily be contiguous in the Markov Model because of the fact that either a "begin struct" or "end struct" state may be present between two adjacent symbols. A pseudo-transition probability is defined between two such non-adjacent states. Therefore, for two such states $q_i$ and $q_j$, the pseudo-transition probability R(i, j) is defined as the transition probability of the unique path from $q_i$ to $q_j$. R(i, j) is denoted as follows:

R(i, j)=$a_{ij}$ if an edge exists between $q_i$ and $q_j$

=$a_{ib} \cdot a_{bj}$ if an edge does not exist between $q_i$ and $q_j$ but $q_b$ is a "begin struct" or "end struct" state and the path $q_i \cdot q_b \cdot q_j$ exists in the model.

The probability of the path $q_{i_0} \ldots q_{i_{T+1}}$ of length T+1 using string segment G is denoted by $P(i_0, i_{T+1}, T+1, G)$. The last symbol of string G is denoted by $g_1$. String G is denoted with its last symbol removed by $G^-$. Thus:

$$P(i_0, i_{T+1}, T+1, G) = \pi_{i_0} R(i_0, i_1) b_{i_1 \theta_1} R(i_1, i_2) b_{i_T-1 \theta_{T-1}} R(i_{T-1}, i_T) b_{i_T \theta_T} R(i_T, i_{T+1})$$

Since $\pi_0 = 1$, it can be ignored. Furthermore, $i_0$ and $i_{T+1}$ are the START and STOP states, whereas the other states need to be chosen in order to maximize the probability of this path. This probability is defined by using the logarithmic probability $\Delta(i_0, i_{T+1}, T+1, G) = \log(P(i_0, i_{T+1}, T+1, G))$. The optimal sequence of intermediate states may be obtained by using an iterative dynamic programming approach. First, a condition to determine $i_T$ is set up which is the Tth intermediate state. This condition expresses a path of length (k+1) in terms of a path of length k. This is achieved in step 620. In general, when the optimal value of $\Delta$ must be found for any pair of nodes p and q for a given path of length n, produces:

$$\Delta(p,q,n,G) = \max_{j-in-S} \Delta(p,j,n-1,G^-) b_{j g_1} R(j,q)$$

Therefore, the above condition is used to execute step 620 by expressing the path of length (n+1) in terms of the path of length n. The corresponding intermediate node j can be computed by taking the argmax value of the above equation. The value of n=1 is special and needs to be set up separately. Thus:

$$\Delta(p,q,1,a) = R(p,q) b_{ja}$$

In step 630, the value of the counter n is increased by 1. The methodology then checks whether n is larger than T in step 640. If n is larger than T, the methodology returns to step 620. If n is not larger than T, the methodology terminates and the current path of length T is reported in step 650 and the process of classification of the test data record terminates.

The model discussed in this invention can be easily extended to a number of different problems. For example, complicated and nested structures, sequential substructures, or multiple labels can be handled by using this model. In each case it is necessary to create a Markov Model. As an example of nested substructures the substructure SE may be embedded within the substructure SS. In this case it is desirable to create the Markov Model so that this known information is taken into account. This general methodology can be utilized for a number of different problems.

Figure 7:
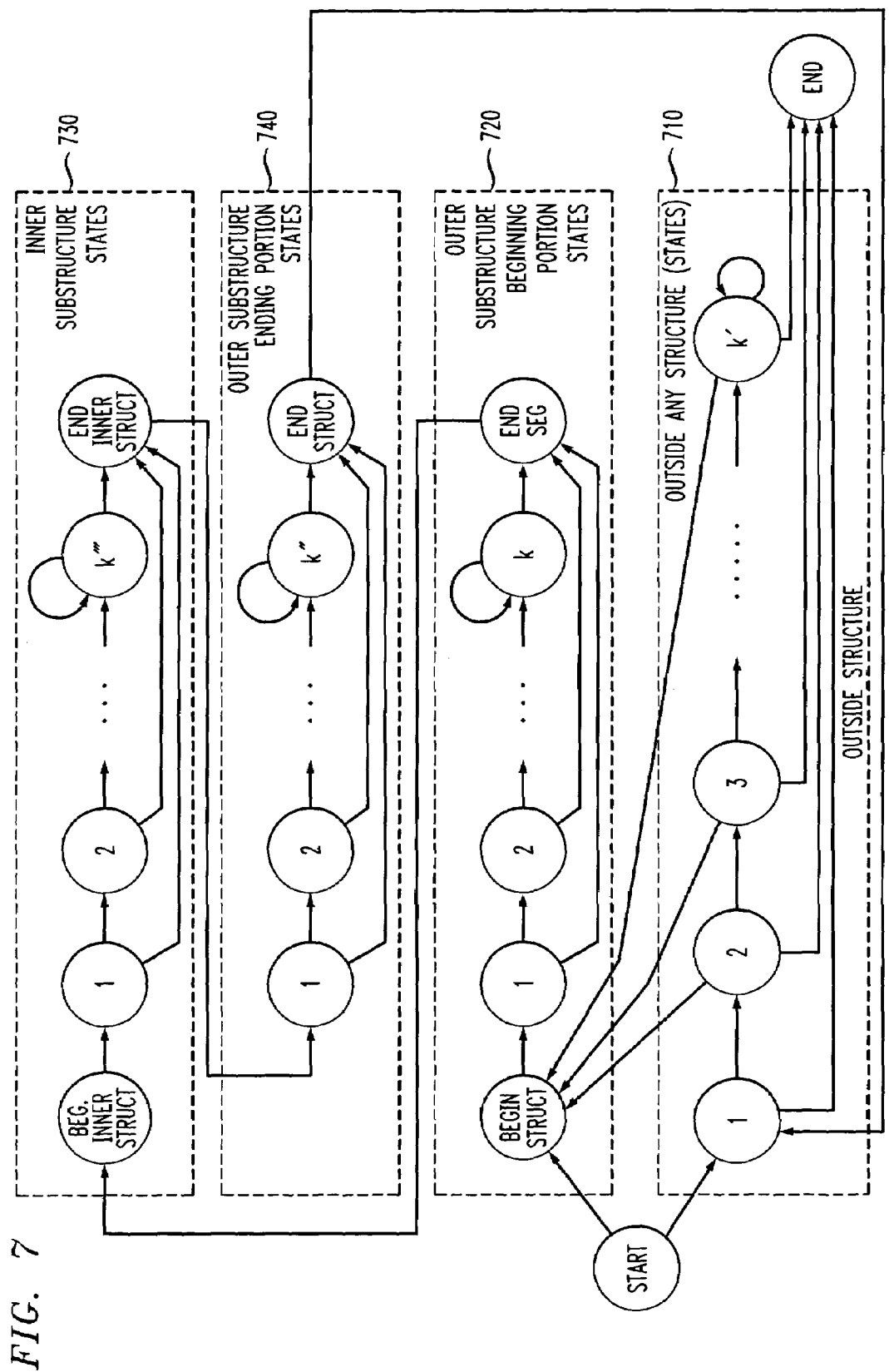
FIG. 7 is a flow diagram illustrating a Markov Model having a simple nesting of two substructures, according to an embodiment of the present invention.

Referring now to FIG. 7, a flow diagram illustrates a Markov Model having a simple nesting of two substructures, according to an embodiment of the present invention. This Markov Model may be constructed in step 310 of FIG. 3 and represents a more complex representation of the model in FIG. 4. The four basic kinds of substructures found in FIG. 7 are:

(1) a first sequence of states outside the substructure SS, 710;

(2) a second sequence of states outside and preceding the substructure SS, but within SE, 720;

(3) a third sequence of states within both SE and SS, 730; and (4) a final sequence of states outside of and succeeding SS, but within SE, 740.

Each set of corresponding states are marked accordingly. The method can be extended automatically to the case of recursive nesting of states.

Figure 8:
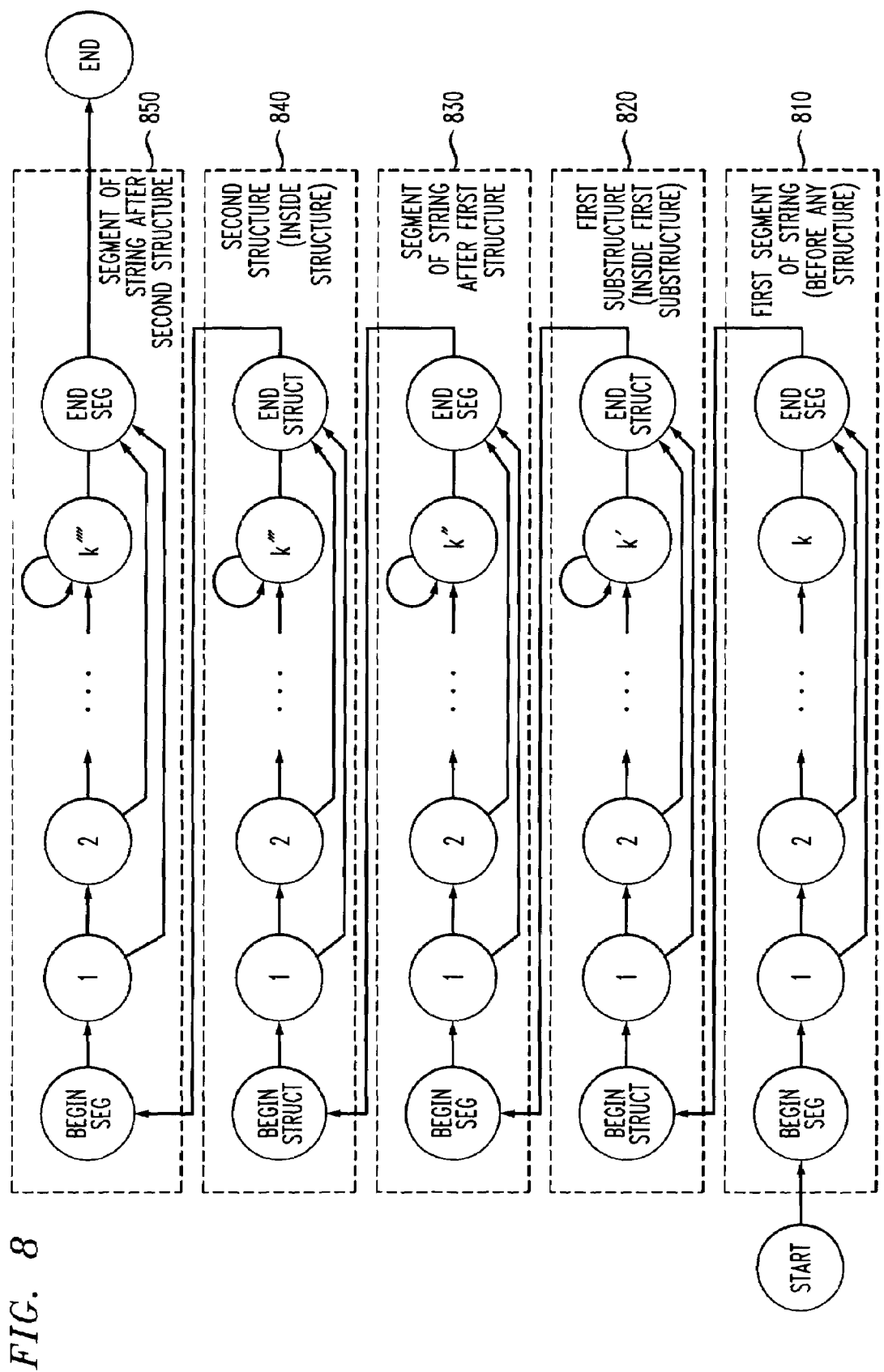
FIG. 8 is a flow diagram illustrating a Markov Model having two sequential substructures, according to an embodiment of the present invention.
Figure 9:
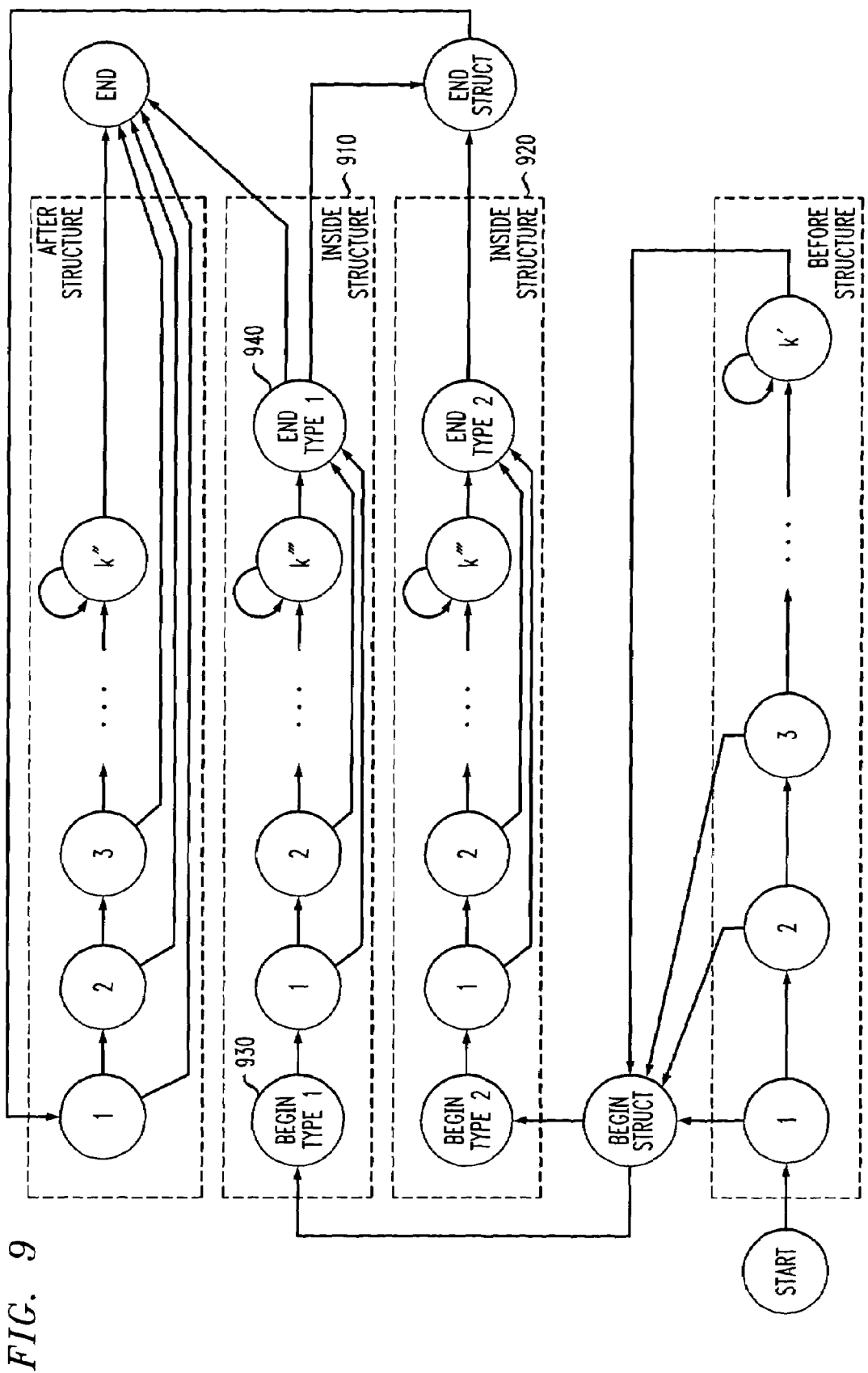
FIG. 9 is a flow diagram illustrating a Markov Model having two types of classes in the strings, according to an embodiment of the present invention.

Referring now to FIG. 8, a flow diagram illustrates a Markov Model having two sequential substructures, according to an embodiment of the present invention. This Markov Model may be constructed in step 310 of FIG. 3 and represents a more complex representation of the model in FIG. 4. Often there may be multiple substructures which may follow one another in the string, referred to as sequential substructures. In combination with the nesting approach discussed above, a powerful tool can be constructed for different categories of structures. Therefore, FIG. 8 shows five distinct sets of states which are ordered from bottom to top:

(1) a first sequence of states before both structures, 810;

(2) a second sequence of states inside the first substructure, 820;

(3) a third sequence of states inside the two substructures, 830;

(4) a fourth sequence of states inside the second substructure, 840; and (5) a final sequence of states after both substructures, 850.

In many cases different kinds of substructures may be present in the same string. In such a case, only a minor modification is needed to the Markov Model of FIG. 4, which is constructed in step 310 of FIG. 3. For the set of states inside the substructure, there may be different possibilities corresponding to the different classes that the structures may be drawn from. For example, referring now to FIG. 9, a flow diagram illustrates a Markov Model having two types of classes in the strings, according to an embodiment of the present invention. These two classes are labeled Type 1, 910, and Type 2, 920, respectively. When the substructure belongs to the class of type 1, 910, then this corresponds to a path through the Markov Model using the states between those labeled "begin type 1," 930, and "end type 1," 940. In this case, the maximum probability path through the Markov Model also provides information on the identity of the class to which the corresponding substructure belongs.

Accordingly, as described herein, the present invention provides techniques for effective string substructure classification. The use of such inventive classification techniques is illustrated above in the context of text. However, the invention is not intended to be limited to use with such an application. Rather, the inventive classification techniques are applicable to a large number of applications such as, by way of further example only, market basket analysis, customer tracking, and DNA analysis.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method of classifying substructures of at least one unmarked string using at least one training data set, comprising the steps of:

constructing a model of class labels and substructures within strings of the at least one training data set, wherein the training data set has markers identifying labeled substructures and the model comprises a plurality of underlying states having transitions in accordance with predefined probabilities;

inserting markers in the at least one unmarked string in accordance with the model, wherein the markers identify substructures in the at least one unmarked string similar to substructures within strings of the at least one training data set; and predicting class labels of substructures in the at least one unmarked string similar to substructures within strings of the at least one training data set in accordance with the model.

2. The method of claim 1, wherein each training data set comprises:

a set of strings, wherein each string comprises at least one marker identifying a beginning of a substructure and at least one marker identifying an end of a substructure; and a set of class labels for association with the substructures.

3. The method of claim 2, wherein each substructure within each training data set comprises:

a begin marker indicating a beginning of the substructure;

an end marker indicating an end of the substructure; and a class label indicating a class of the substructure.

4. The method of claim 3, wherein a model for a simple structural embedding comprises three sets of states: (a) a set of states for a portion of the string before the begin marker; (b) a set of states for a portion of the string within the begin marker and end marker; and (c) a set of states for a portion of the string after the end marker.

5. The method of claim 1, wherein the at least one unmarked string comprises a first inner substructure nested within a second outer substructure.

6. The method of claim 5, wherein a model for the first inner substructure nested within the second outer substructure has five sets of states: (a) a set of states for a portion of the string before both the inner substructure and the outer substructure; (b) a set of states for a portion of the string within the outer substructure, but before the inner substructure; (c) a set of states for a portion of the string within both the inner substructure and the outer substructure; (d) a set of states for a portion of the string within the outer substructure, but after the inner substructure; and (e) a set of states for a portion of the string after both the inner substructure and the outer substructure.

7. The method of claim 1, wherein the at least one unmarked string comprises sequentially occurring substructures.

8. The method of claim 7, wherein the model for sequentially occurring substructures within a string has different sets of states for each sequential substructure.

9. The method of claim 1, wherein the at least one unmarked string comprises substructures having different class labels.

10. The method of claim 9, wherein the model for the at least one unmarked string with substructures having different class labels has a different set of states for each class label.

11. The method of claim 1, wherein the step of constructing a model comprises modeling a relationship of substructures in strings of the at least one training data set using a stochastic model.

12. The method of claim 11, further comprising the step of generating a symbol having a probability of performing a transition from one of a number of states to another in the stochastic model.

13. The method of claim 12, further comprising the step of determining the number of states in the model using the at least one training data set.

14. The method of claim 13, wherein the number of states in the model is a function of a length of the strings in the model.

15. The method of claim 12, further comprising the step of determining the probability of transition from one state to another using the at least one training data set.

16. The method of claim 15, wherein the probability of transition from one state to another is a function of a percentage of transition between the states using the at least one training data set.

17. The method of claim 12, further comprising the step of determining the probability of generation of the symbols at a given state using the at least one training data set.

18. The method of claim 17, wherein the step of determining the probability of generation of the symbols at a given state comprises using a probability of generation of each symbol at a given state in the at least one training data set.

19. The method of claim 11, wherein each string corresponds to a path in the stochastic model.

20. The method of claim 19, wherein a probability of the path corresponds to a level of correlation of the model to the string.

21. The method of claim 1, wherein the step of inserting markers in the at least one unmarked string comprises inserting markers in such a way that a corresponding path in a stochastic model has a maximum probability.

22. Apparatus for classifying substructures of at least one unmarked string, using at least one training data set, comprising:
a memory; and
at least one processor, coupled to the memory, operative to: (i) construct a model of class labels and substructures within strings of the at least one training data set, wherein the training data set has markers identifying labeled substructures and the model comprises a plurality of underlying states having transitions in accordance with predefined probabilities; (ii) insert markers in the at least one unmarked string in accordance with the model, wherein the markers identify substructures in the at least one unmarked string similar to substructures within strings of the at least one training data set; and (iii) predict class labels of substructures in the at least one unmarked string similar to substructures within strings of the at least one training data set in accordance with the model.

23. The apparatus of claim 22, wherein each training data set comprises:
a set of strings, wherein each string comprises at least one marker identifying a beginning of a substructure and at least one marker identifying an end of a substructure; and
a set of class labels for association with the substructures.

24. The apparatus of claim 23, wherein each substructure within each training data set comprises:
a begin marker indicating a beginning of the substructure;
an end marker indicating an end of the substructure; and
a class label indicating a class of the substructure.

25. The apparatus of claim 24, wherein a model for a simple structural embedding comprises three sets of states: (a) a set of states for a portion of the string before the begin marker; (b) a set of states for a portion of the string within the begin marker and end marker; and (c) a set of states for a portion of the string after the end marker.

26. The apparatus of claim 22, wherein the at least one unmarked string comprises a first inner substructure nested within a second outer substructure.

27. The apparatus of claim 26, wherein a model for the first inner substructure nested within the second outer substructure has five sets of states: (a) a set of states for a portion of the string before both the inner substructure and the outer substructure; (b) a set of states for a portion of the string within the outer substructure, but before the inner substructure; (c) a set of states for a portion of the string within both the inner substructure and the outer substructure; (d) a set of states for a portion of the string within the outer substructure, but after the inner substructure; and (e) a set of states for a portion of the string after both the inner substructure and the outer substructure.

28. The apparatus of claim 22, wherein the at least one unmarked string comprises sequentially occurring substructures.

29. The apparatus of claim 28, wherein the model for sequentially occurring substructures within a string has different sets of states for each sequential substructure.

30. The apparatus of claim 22, wherein the at least one unmarked string comprises substructures having different class labels.

31. The apparatus of claim 30, wherein the model for the at least one unmarked string with substructures having different class labels has a different set of states for each class label.

32. The apparatus of claim 22, wherein the operation of constructing a model comprises modeling a relationship of substructures in strings of the at least one training data set using a stochastic model.

33. The apparatus of claim 32, wherein the at least one processor is further operative to generate a symbol having a probability of performing a transition from one of a number of states to another in the stochastic model.

34. The apparatus of claim 33, wherein the at least one processor is further operative to determine the number of states in the model using the at least one training data set.

35. The apparatus of claim 34, wherein the number of states in the model is a function of a length of the strings in the model.

36. The apparatus of claim 33, wherein the at least one processor is further operative to determine the probability of transition from one state to another using the at least one training data set.

37. The apparatus of claim 36, wherein the probability of transition from one state to another is a function of a percentage of transition between the states using the at least one training data set.

38. The apparatus of claim 33, wherein the at least one processor is further operative to determine the probability of generation of the symbols at a given state using the at least one training data set.

39. The apparatus of claim 38, wherein the operation of determining the probability of generation of the symbols at a given state comprises using a probability of generation of each symbol at a given state in the at least one training data set.

40. The apparatus of claim 32, wherein each string corresponds to a path in the stochastic model.

41. The apparatus of claim 40, wherein a probability of the path corresponds to a level of correlation of the model to the string.

42. The apparatus of claim 22, wherein the operation of inserting markers in the at least one unmarked string comprises inserting markers in such a way that a corresponding path in a stochastic model has a maximum probability.

43. An article of manufacture for classifying substructures of at least one unmarked string, using at least one training data set, comprising a machine readable medium containing one or more programs which when executed implement the steps of:

constructing a model of class labels and substructures within strings of the at least one training data set, wherein the training data set has markers identifying labeled substructures and the model comprises a plurality of underlying states having transitions in accordance with predefined probabilities;

inserting markers in the at least one unmarked string in accordance with the model, wherein the markers identify substructures in the at least one unmarked string similar to substructures within strings of the at least one training data set; and predicting class labels of substructures in the at least one unmarked string similar to substructures within strings of the at least one training data set in accordance with the model.

* * * * *